US010426635B2

(12) United States Patent
Bader et al.

(10) Patent No.: US 10,426,635 B2
(45) Date of Patent: Oct. 1, 2019

(54) MEDICAL FORCE MEASURING SYSTEM

(71) Applicant: Aesculap AG, Tuttlingen (DE)

(72) Inventors: Uwe Bader, Tuttlingen (DE); Mevluet Sungu, Schaffhausen (CH)

(73) Assignee: Aesculap AG, Tuttlingen (DE)

( * ) Notice: Subject to any disclaimer, the term of this patent is extended or adjusted under 35 U.S.C. 154(b) by 743 days.

(21) Appl. No.: 14/972,856

(22) Filed: Dec. 17, 2015

(65) Prior Publication Data

US 2016/0175116 A1  Jun. 23, 2016

(30) Foreign Application Priority Data

Dec. 22, 2014 (DE) .................. 10 2014 119 348

(51) Int. Cl.
*A61F 2/46* (2006.01)
*A61F 2/34* (2006.01)
*A61F 2/36* (2006.01)

(52) U.S. Cl.
CPC .......... *A61F 2/4657* (2013.01); *A61F 2/4684* (2013.01); *A61F 2/34* (2013.01); *A61F 2002/365* (2013.01); *A61F 2002/3611* (2013.01); *A61F 2002/4666* (2013.01)

(58) Field of Classification Search
CPC .. A61F 2002/4666; A61F 2/34; A61F 2/4609; A61F 2002/3611; A61F 2002/365
See application file for complete search history.

(56) References Cited

U.S. PATENT DOCUMENTS

| 3,053,251 A | * | 9/1962 | Black | A61F 2/3603 623/23.12 |
| 3,818,512 A | * | 6/1974 | Shersher | A61F 2/30739 623/22.15 |
| 4,032,994 A | * | 7/1977 | Frey | A61F 2/32 623/22.45 |
| 4,687,488 A | * | 8/1987 | Frey | A61F 2/3609 623/22.45 |
| 4,842,605 A | * | 6/1989 | Sonnerat | A61F 2/3609 623/22.45 |

(Continued)

FOREIGN PATENT DOCUMENTS

| DE | 102008030261 | 12/2009 |
| WO | 2013/170573 | 11/2013 |
| WO | 2014/071193 | 5/2014 |

*Primary Examiner* — David W Bates
(74) *Attorney, Agent, or Firm* — Lipsitz & McAllister, LLC

(57) ABSTRACT

A medical force measuring system is provided for measuring a force effective between two prosthesis parts that are connected to one another in articulated manner in a joint prosthesis which includes a ball joint or a partial component thereof. The force measuring system includes a measuring instrument which has a sample joint element with a sample joint surface. The sample joint element is formed in correspondence with a first joint element that forms a part of the ball joint and has a joint surface which is formed in correspondence with the sample joint surface and is moveable into engagement therewith for forming a sample ball joint. The measuring instrument also includes at least one of a measuring device and an indicating device which cooperates with the sample joint element for measuring and/or indicating a force (or a partial component thereof) effective on the sample joint surface.

19 Claims, 12 Drawing Sheets

(56) References Cited

U.S. PATENT DOCUMENTS

| | | | | |
|---|---|---|---|---|
| 4,922,898 A * | 5/1990 | Dunn | A61F 2/4607 | 606/80 |
| 5,362,311 A * | 11/1994 | Amino | A61F 2/3609 | 623/22.45 |
| 6,176,140 B1 * | 1/2001 | Autenrieth | A61F 2/34 | 623/908 |
| 6,336,941 B1 * | 1/2002 | Subba Rao | A61F 2/3609 | 623/22.42 |
| 6,447,448 B1 * | 9/2002 | Ishikawa | A61B 5/0031 | 600/300 |
| 6,527,808 B1 * | 3/2003 | Albertorio | A61F 2/32 | 623/22.24 |
| 6,564,647 B1 * | 5/2003 | Richter | A61F 2/468 | 73/818 |
| 6,585,771 B1 * | 7/2003 | Buttermilch | A61F 2/4637 | 623/21.11 |
| 6,610,096 B2 * | 8/2003 | MacDonald | A61B 5/076 | 623/18.11 |
| 6,706,071 B1 * | 3/2004 | Wolter | A61F 2/30742 | 623/22.13 |
| 6,863,692 B2 * | 3/2005 | Meulink | A61F 2/0095 | 206/363 |
| 7,458,989 B2 * | 12/2008 | Banks | A61B 5/6846 | 600/300 |
| 7,947,220 B2 * | 5/2011 | Lambert | A61L 2/206 | 134/22.15 |
| 8,128,708 B2 * | 3/2012 | Hiles | A61L 2/0088 | 602/50 |
| 8,226,728 B2 * | 7/2012 | Preuss | A61F 2/34 | 623/22.14 |
| 8,361,162 B2 * | 1/2013 | Berry | A61F 2/30724 | 623/22.12 |
| 8,764,845 B2 * | 7/2014 | Brooks | A61F 2/30 | 623/23.11 |
| 9,216,086 B2 * | 12/2015 | Conrad | A61F 2/4684 | |
| 9,248,021 B1 * | 2/2016 | Termanini | A61F 2/30721 | |
| 9,615,927 B2 * | 4/2017 | Huff | A61F 2/3609 | |
| 9,770,336 B2 * | 9/2017 | Forsell | A61F 2/3603 | |
| 10,034,779 B2 * | 7/2018 | Chen | A61F 2/4657 | |
| 2004/0226343 A1 * | 11/2004 | Babler | A61F 2/468 | 73/37 |
| 2007/0005145 A1 | 1/2007 | Banks et al. | | |
| 2009/0299484 A1 * | 12/2009 | Dietrich | A61F 2/0095 | 623/22.4 |
| 2014/0094927 A1 * | 4/2014 | Weeden | A61F 2/32 | 623/22.21 |
| 2014/0350691 A1 * | 11/2014 | Linares | A61F 2/3609 | 623/22.45 |
| 2015/0289890 A1 | 10/2015 | Chen et al. | | |
| 2015/0297362 A1 * | 10/2015 | Singh | A61F 2/4657 | 623/22.15 |

\* cited by examiner

MEDICAL FORCE MEASURING SYSTEM

CROSS-REFERENCE TO RELATED APPLICATIONS

This application claims the benefit of German patent application number 10 2014 119 348.2 filed on Dec. 22, 2014, which is incorporated by reference herein in its entirety and for all purposes.

FIELD OF THE INVENTION

The present invention relates to medical force measuring systems generally, and more specifically to a medical force measuring system for measuring a force that is effective between two prosthesis parts that are connected to one another in articulated manner in a joint prosthesis comprising a ball joint or a partial component thereof, which force measuring system comprises a measuring instrument, which measuring instrument comprises a sample joint element having a sample joint surface, which sample joint element is formed in correspondence with a first joint element that forms a part of the ball joint and comprises a joint surface that is formed in correspondence with the sample joint surface and is moveable into engagement therewith for forming a sample ball joint.

BACKGROUND OF THE INVENTION

Medical force measuring systems for measuring forces of the type described hereinabove are not so far known. However, sample implant systems such as are described in DE 10 2008 030 261 A1 in particular are known. Nevertheless, such sample implant systems do not enable the influence of the soft parts surrounding the artificial joint upon the stability thereof to be determined. This can be particularly important for determining and, where necessary, reducing the tendency of the artificial joint to become dislocated.

SUMMARY OF THE INVENTION

In a first aspect of the invention, a medical force measuring system for measuring a force that is effective between two prosthesis parts that are connected to one another in articulated manner in a joint prosthesis comprising a ball joint or a partial component thereof is provided. Said force measuring system comprises a measuring instrument. Said measuring instrument comprises a sample joint element having a sample joint surface. Said sample joint element is formed in correspondence with a first joint element that forms a part of the ball joint and comprises a joint surface that is formed in correspondence with the sample joint surface and is moveable into engagement therewith for forming a sample ball joint. Said measuring instrument comprises at least one of a measuring device and an indicating device which cooperates with the sample joint element for at least one of measuring and indicating a force that is effective on the sample joint surface or a partial component of the force that is effective on the sample joint surface.

BRIEF DESCRIPTION OF THE DRAWINGS

The foregoing summary and the following description may be better understood in conjunction with the drawing figures, of which.

DETAILED DESCRIPTION OF THE INVENTION

Figure 1:
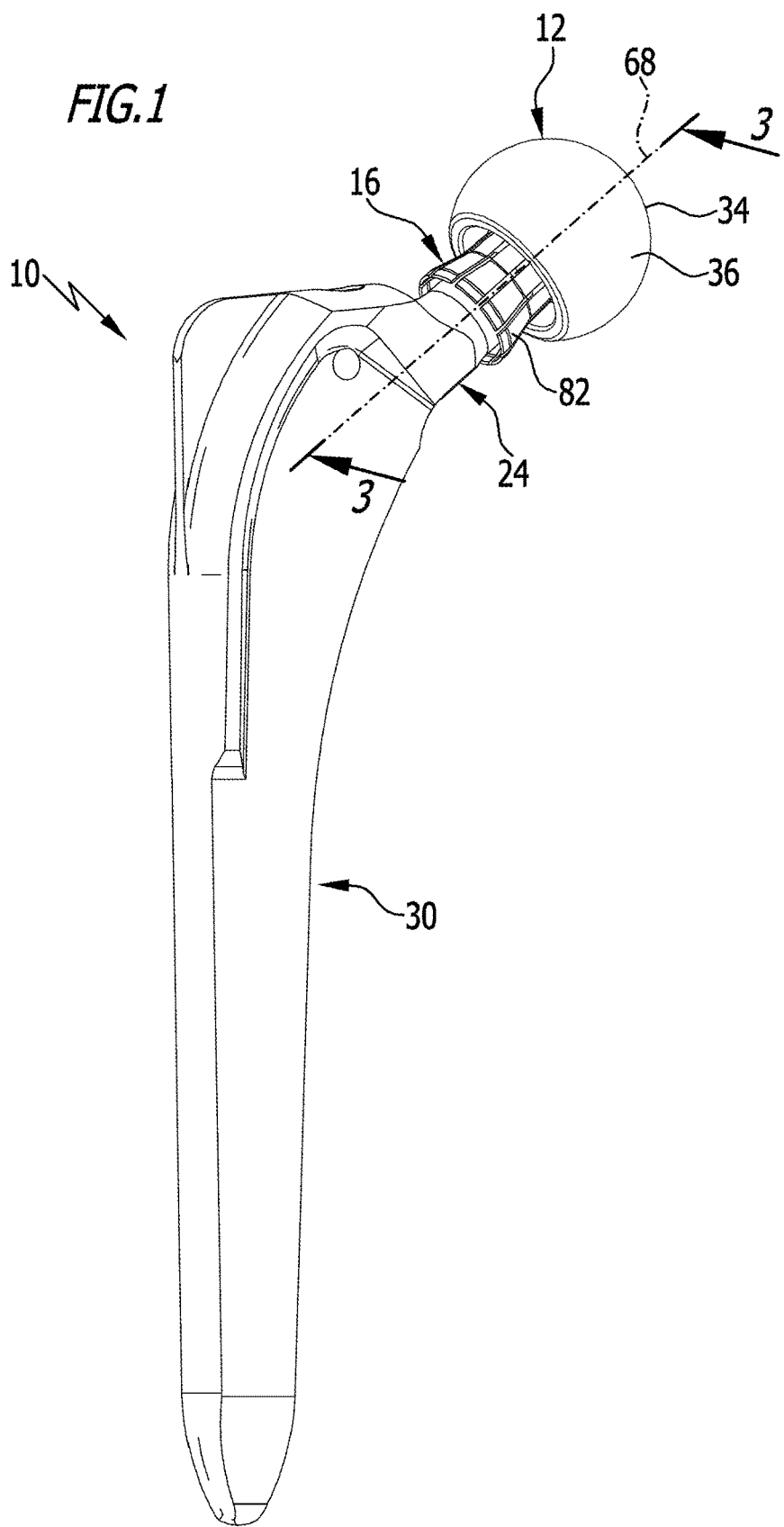
FIG. 1: shows a perspective overall view of a first embodiment of a force measuring system.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical force measuring system for measuring a force that is effective between two prosthesis parts that are connected to one another in articulated manner in a joint prosthesis comprising a ball joint or a partial component thereof, which force measuring system comprises a measuring instrument, which measuring instrument comprises a sample joint element having a sample joint surface, which sample joint element is formed in correspondence with a first joint element that forms a part of the ball joint and comprises a joint surface that is formed in correspondence with the sample joint surface and is moveable into engagement therewith for forming a sample ball joint, wherein the measuring instrument comprises at least one of a measuring device and an indicating device which cooperates with the sample joint element for at least one of measuring and indicating a force that is effective on the sample joint surface or a partial component of the force that is effective on the sample joint surface.

With the aid of such a medical force measuring system, it is thereby possible, in particular, for a doctor who is implanting the joint prosthesis to detect so-called poor "balancing" of the soft parts. Even if the joint geometry is reconstructed as it was originally on the basis of a pre-operative design, an imbalance of the joint forces that are effective on the joint prosthesis can nevertheless occur due to the selected point of access to the site of the operation or a change in the antetorsion. In particular, the force measuring system enables the doctor to be given feedback intra-operatively in regard to the resulting force that is effective on the sample joint surface. This is particularly advantageous because the "balancing" of the soft parts has an influence on the stability of the joint. If the force in the form of a force vector comprising the sum of all the forces affecting the joint that are applied in particular by the muscles is unfavourable, then this has an influence on the tendency for a dislocation to occur. In the case of a hip joint for example, this can have an effect upon the long-term success of the implant and in particular on that of the joint socket. Post-operatively, a force-imbalance in the forces of the surrounding soft parts that are effective on the hip joint can occur, namely in particular, due to the separation, damage or detachment of muscle parts but also due to altered geometrical dimensions in the joint itself. Post-operatively occurring hip pains can, for example, be the consequence of failed osseous-integration of the implant or even the cause thereof may lie in the aforesaid force imbalance which alters the forces occurring in the individual muscles in comparison with the state prior to surgery, something which can cause a non-physiological situation of the pain in the joint. Especially in the case where the pain persists for a long time after surgery, relief of the relevant muscles by a partial separation process has to be tried in a further operation. The medical force measuring system enables the surgeon to detect the imbalance intra-operatively and then take the necessary counter measures so as to avoid insofar as possible the need for such a revision operation because of the imbalance of the forces.

It is expedient if the measuring instrument comprises a measuring instrument coupling device for temporarily coupling in force- and/or positive-locking manner to a coupling device of a prosthesis part of the joint prosthesis or a medical instrument. The measuring instrument coupling device makes it possible in particular to couple the measuring instrument temporarily to a prosthesis part such as a hip shaft or an acetabulum of an artificial hip joint for example or to a medical instrument. The measuring instrument can then be temporarily coupled to the prosthesis part or to a medical instrument by its sample joint element together with a previously implanted joint element of the joint prosthesis that is to be implanted for the purposes of forming a sample ball joint.

Advantageously, the medical force measuring system comprises a medical instrument which comprises the measuring instrument or is couplable to the measuring instrument. In particular, the measuring instrument can already be arranged on the medical instrument. Alternatively, it could also be couplable temporarily to the measuring instrument. This makes it possible in particular to couple the measuring instrument selectively to the instrument and, if necessary, to a prosthesis part of the joint prosthesis during the implantation process.

It is expedient if the medical instrument is in the form of a rasp or a rasp shaft. For example, a bone cavity for the insertion of a prosthesis shaft of a hip joint endoprosthesis can be prepared in a femur with the aid of a rasp. A force on the sample joint surface of the measuring instrument coupled to the rasp or the rasp shaft can then be determined for example when the rasp or the rasp shaft is placed in the bone cavity.

In order to produce a simple connection of the medical instrument to the measuring instrument, it is expedient if the medical instrument comprises an instrument coupling device which is moveable into engagement with the measuring instrument coupling device in force- and/or positive-locking manner.

The medical instrument and the measuring instrument can be coupled to one another in a particularly simple way if the instrument coupling device or the measuring instrument coupling device is in the form of a coupling projection and if the respective other coupling device is in the form of a coupling seating corresponding to the coupling projection. For example, the instrument may comprise a coupling projection or a coupling seating, and the measuring instrument may likewise comprise a coupling projection or a coupling seating.

In accordance with a further preferred embodiment of the invention, provision may be made for the coupling projection to be arranged or formed on the prosthesis part or on the instrument and for the coupling seating to be arranged or formed on the measuring instrument, or, for the coupling seating to be arranged or formed on the prosthesis part or on the instrument and the coupling projection to be arranged or formed on the measuring instrument. In particular, the just described further development enables the measuring instrument to be in the form of or part of a sample ball head or else, in the form of part of a sample joint socket or a sample joint socket insert of a hip joint endoprosthesis.

Preferably, the medical force measuring system comprises a prosthesis part of the joint prosthesis which is couplable temporarily to the measuring instrument. For example hereby, it may be the prosthesis part that is to be implanted permanently or a sample prosthesis part which is used only temporarily during the surgical procedure.

It is advantageous, particularly for the implantation of a hip joint endoprosthesis, if the prosthesis part is in the form of a prosthesis shaft that is implantable into a bone cavity or is in the form of a joint socket or a joint socket insert of a joint socket.

It is expedient if the sample joint element is in the form of a sample joint head or in the form of a socket insert of a hip joint prosthesis. This makes it possible in particular for a surgeon to temporarily couple the sample joint element in the form of a sample joint head to a previously implanted joint socket in order to determine the soft-part-forces that are effective on the joint. Alternatively, the sample joint element in the form of a socket insert of a hip joint prosthesis could also be coupled temporarily to a joint head of a shaft that was previously implanted in a bone cavity in order to determine the resultant of the effective soft-part-forces.

The force measuring system can be utilised in a particularly versatile manner if the measuring instrument comprises a coupling element and if the coupling element comprises the measuring instrument coupling device. In particular, the measuring instrument can then be constructed in two-piece or multipart form if it comprises the sample joint element and the coupling element and possibly yet further parts or elements.

In order to enable the forces that are effective between the sample joint element and the coupling element to be determined in a simple manner, it is expedient if the sample joint element and the coupling element are arranged to be moveable relative to each other or are mounted on one another or are formed such as to be moveable relative to each other. In particular, an effective force which is effective on the sample joint surface can then be measured mechanically in order to move the sample joint element relative to the coupling element.

Preferably, the sample joint element and the coupling element are arranged or formed to be displaceable and/or rotatable relative to each other. In particular, the sample joint element and the coupling element can be arranged or formed such that they are moveable relative to each other in all directions in space. It is also conceivable to totally or partly limit this to one, two or three degrees of freedom of movement of the sample joint element and the coupling element.

The measuring instrument can be coupled temporarily to a prosthesis part or to a medical instrument in particularly simple way if the instrument coupling device comprises a clamping element which is moveable into engagement in force- and/or positive-locking manner with the prosthesis part or the medical instrument on the one hand and with the coupling element on the other.

The force measuring system can be constructed in a particularly compact manner if the clamping element is in the form of a clamping ring which, in a clamping position, engages in an annular groove in the prosthesis part or in the instrument on the one hand and/or in an annular groove in the coupling element. For example, the measuring instrument can be placed on a neck of the medical instrument, the neck of a rasp for example, or on a neck of a prosthesis shaft and then held there in clamped manner.

In order to facilitate the connection of the measuring instrument to a prosthesis part or to an instrument, it is expedient if the clamping element is resilient and/or flexible.

In order to enable an effective force to be indicated to a surgeon intra-operatively, it is advantageous if the indicating device comprises at least one indicating element and at least one reference element and if the at least one indicating element and the at least one reference element are arranged or formed such as to be moveable relative to each other. In particular, such an indicating device enables a movement or a deflection of the at least one indicating element and the at least one reference element relative to each other to be made directly visible or apparent to a surgeon. The indicating device can, in particular, be purely mechanical so that no further elements are necessary for indicating an effective force or a partial component thereof.

Furthermore, it can be expedient if the indicating device comprises a plurality of indicating elements which are deflectable from a basic position and/or are temporarily deformable as a result of an application of force to the sample joint element and/or the coupling element. In particular, the plurality of indicating elements can be arranged in such a manner that a deflection or a deformation of one or more of the indicating elements immediately permits a conclusion to be drawn as to the direction and possibly to the magnitude of a force that is effective on the sample joint element and in particular on the sample joint surface thereof.

The measuring instrument can be constructed in a particularly simple way if the plurality of indicating elements are in the form of curved lamellas which project from the coupling element and are directed away from the sample joint element. In particular, the lamellas can be arranged in such a manner that one or more of the lamellas are deflected and/or deformed in the event of a relative movement between the coupling element and the sample joint element.

In order to enable the orientation of the effective force to be indicated in a simple manner, it is advantageous if the plurality of indicating elements are arranged or formed to surround the coupling seating in the circumferential direction. For example, the direction of the effective force or at least a partial component thereof can then be indicated directly by a deflection or a deformation of one or more of the indicating elements.

It is expedient if the coupling element defines a longitudinal axis of the coupling element and if the plurality of indicating elements is arranged to surround the longitudinal axis of the coupling element. In particular, the plurality of indicating elements can be arranged or formed such as to surround the longitudinal axis of the coupling element uniformly in the circumferential direction. Thus in particular, a force or a component of the force which is effective between the sample joint element and the coupling element for example can be indicated with reference to the longitudinal axis of the coupling element.

In order to improve the operation of the medical force measuring system, it is advantageous if the coupling element and the sample joint element are coupled to one another in force- and/or positive-locking manner. In particular, the coupling element and the sample joint element can be prevented from not being unintentionally separated from each other in this way.

The coupling element and the sample joint element can be connected to one another in a particularly simple way if they are coupled to one another by a clamping or latching process. To this end, there are provided clamping elements or else cooperating and/or inter-engaging parts of the coupling element and the sample joint element. In particular, a connection of the coupling element and the sample joint element can also be established by means of a press-fit. Optionally or as an alternative thereto, latching elements that are in force- and/or positive-locking engagement with one another in a connecting position could also be arranged or formed on the coupling element and on the sample joint element.

In accordance with a further preferred embodiment of the invention, provision may be made for the at least one indicating element to be in the form of an annular surface on the sample joint element or on the coupling element and for the at least one reference element to be in the form of a ring which is of smaller diameter than the annular surface and at least partly covers it. This arrangement makes it possible in particular to form an indicating device which renders a relative movement between the ring and the annular surface visible. For example, if a force is effective on the sample joint element, then this can be optionally moved relative to the coupling element, whereby the ring and the annular surface are then likewise moved relative to each other. A shift in the alignment between the ring and the annular surface, which are concentric in a basic position, enables a surgeon to immediately recognize the direction from which or the direction in which a force is being applied to the sample joint element by the soft parts.

The measuring instrument can be constructed in a particularly simple way if the annular surface is in the form of a flat end face which faces away from the sample joint element and surrounds a recess in the sample joint element with which the coupling element engages, and if the coupling element comprises a ring flange that surrounds the coupling seating and is directed radially away from a longitudinal axis of the coupling seating and also forms the ring. A deflection of the sample joint element and the coupling element relative to each other can thus be rendered visible in a simple manner, namely, when the annular surface, which is visible in the basic position as being concentric with the longitudinal axis of the coupling seating and is partly covered by the ring in this basic position, adopts a visibly non-round shape due to a relative movement between the sample joint element and the coupling element.

It is expedient if the coupling element and the sample joint element are axially fixed relative to each other taken with respect to the longitudinal axis of the coupling element. Thus in particular, the sample joint element and the coupling element can then be prevented from being unintentionally separated from each other parallel to the longitudinal axis of the coupling element.

In order to improve the mobility of the measuring instrument, it is advantageous if the coupling element and the sample joint element are coupled such as to be rotatable relative to each other about the longitudinal axis of the coupling element. Optionally, they could also be arranged or formed to be displaceable relative to each other in a plane which runs perpendicularly or transversely of the longitudinal axis of the coupling element.

Preferably, the coupling element and the sample joint element comprise cooperating coupling members which inter-engage in positive or substantially positive manner. For example, these may be cooperating projections and recesses which are arranged or formed on the sample joint element on the one hand or on the coupling element on the other.

In order to permit movement in a plane perpendicular or transverse to the longitudinal axis of the coupling element in particular, it is advantageous if the cooperating coupling members comprise an annular groove and a corresponding ring flange which are arranged or formed on the coupling element on the one hand and on the sample joint element on the other.

It is expedient if a minimum internal diameter of the annular groove is larger than a maximum external diameter of the ring flange. A desired amount of play or a desired degree of movement of the ring flange in the annular groove can then be provided in a simple manner.

In order to achieve secure coupling on the one hand and as unrestricted mobility as possible on the other in a desired way, it is advantageous if the height of the ring flange in the radial direction is greater than half the depth of the annular groove in the radial direction.

In accordance with a further preferred embodiment of the invention, provision may be made for the measuring device to comprise at least one force measuring sensor for measuring the magnitude and/or direction of a force effective thereon. In particular, two, three or more force measuring sensors could also be provided.

The measuring instrument can be constructed in a particularly simple and compact manner if the at least one force measuring sensor is arranged between the sample joint element and the coupling element. A relative force which is effective between the coupling element and the sample joint element can then be measured in a simple manner.

In order to improve the accuracy of the measurement of the force that is to be determined, it is advantageous for a plurality of force measuring sensors to be provided.

Expediently, the at least one force measuring sensor is arranged on one of the cooperating coupling members. This enables the measuring instrument to be of particularly compact construction.

In order to enable the at least one force measuring sensor to be arranged in a secure and defined manner, it is advantageous if at least one of the coupling members comprises at least one sensor seating for accommodating the at least one force measuring sensor. In particular, the sensor seating can be formed in such a way that the at least one force measuring sensor engages therein in force- and/or positive-locking manner, or is held in the sensor seating so as to be moveable in a defined manner.

The measuring device can be constructed in a particularly compact manner if the at least one sensor seating is arranged or formed in the ring flange.

Preferably, the at least one force measuring sensor is in the form of an electronic force measuring sensor for producing an electrical measuring signal. The measuring signal can be further processed in any appropriate manner, for example, with a computer. The force measuring sensor can be in the form of a digital or analogue force measuring sensor which can produce an analogue or digital electrical measuring signal.

In accordance with a further preferred embodiment of the invention, provision may be made for the at least one force measuring sensor to comprise a transmitting device for sending a measuring signal to a receiving device of a signal indicator device for evaluating and/or displaying the measuring signal. Such a transmitting device enables the measuring signal to be fed to the receiving device of the signal indicator device in order to further process it and if necessary display it there.

A surgeon can recognize a force imbalance in the region of the joint that is to be implanted in a simple manner if the signal indicator device comprises a screen. In particular, a force can then be portrayed on the screen in accord with the particular magnitude and/or orientation thereof so that the necessary measures for the establishment of the desired force equilibrium can be taken.

It is advantageous if the transmitting device and/or the receiving device are designed for the transmission of the measuring signal to be effected over cables or a non-cable connection. In particular, a non-cable connection transmission can be achieved by means of a near field communication interface device over radio or Bluetooth or the like.

The production of the medical force measuring system can be further simplified if the sample joint element is formed in one piece manner and/or if the coupling element is formed in one piece manner. The force measuring instrument in particular, can then be formed of only two parts.

A first exemplary embodiment of a medical force measuring system bearing the general reference symbol 10 is illustrated in exemplary manner in FIGS. 1 to 5. It comprises a measuring instrument 12 incorporating a sample joint element 14 and a coupling element 16.

The medical force measuring system 10 is designed for measuring a force effective between two prosthesis parts 24 and 26 that are connected to one another in articulated manner in a joint prosthesis 18 comprising a ball joint or a partial component 22 of the joint prosthesis 18.

In the exemplary embodiment that is schematically illustrated in FIGS. 1 to 5, the joint prosthesis 18 is in the form of a hip joint endoprosthesis 28 incorporating a shaft 30 which is insertible into a bone cavity of a femur and comprises a neck 32 at its proximal end which is couplable temporarily to the measuring instrument 12. Optionally, the joint prosthesis 18 could also be formed in modular manner so that the shaft 30 and the neck of 32 are each in the form of separate prosthesis parts which are couplable to one another as desired in dependence on the size of a patient.

The sample joint element 14 is in the form of a sample joint head 34 having a spherical sample joint surface 36. The sample joint surface 36 is formed such as to correspond to a joint surface 38 of the prosthesis part 26. In the exemplary embodiment illustrated in the Figures, the prosthesis part 26 is in the form of an acetabulum 40 which is implantable into a pelvic bone using a socket insert 42 that is fixable therein in force- and/or positive-locking manner, wherein the socket insert 42 comprises the hollow spherical joint surface 38.

Optionally, the measuring instrument 12 could also be designed for coupling to a medical instrument in the form of a rasp or a rasp shaft for example which is used for preparing the bone cavity for the insertion of the shaft 30. At the proximal end thereof, the rasp shaft or the rasp has an instrument coupling device in the form of a neck similar to the neck 32 so that the measuring instrument 12 is also couplable temporarily to the medical instrument.

Figure 3:
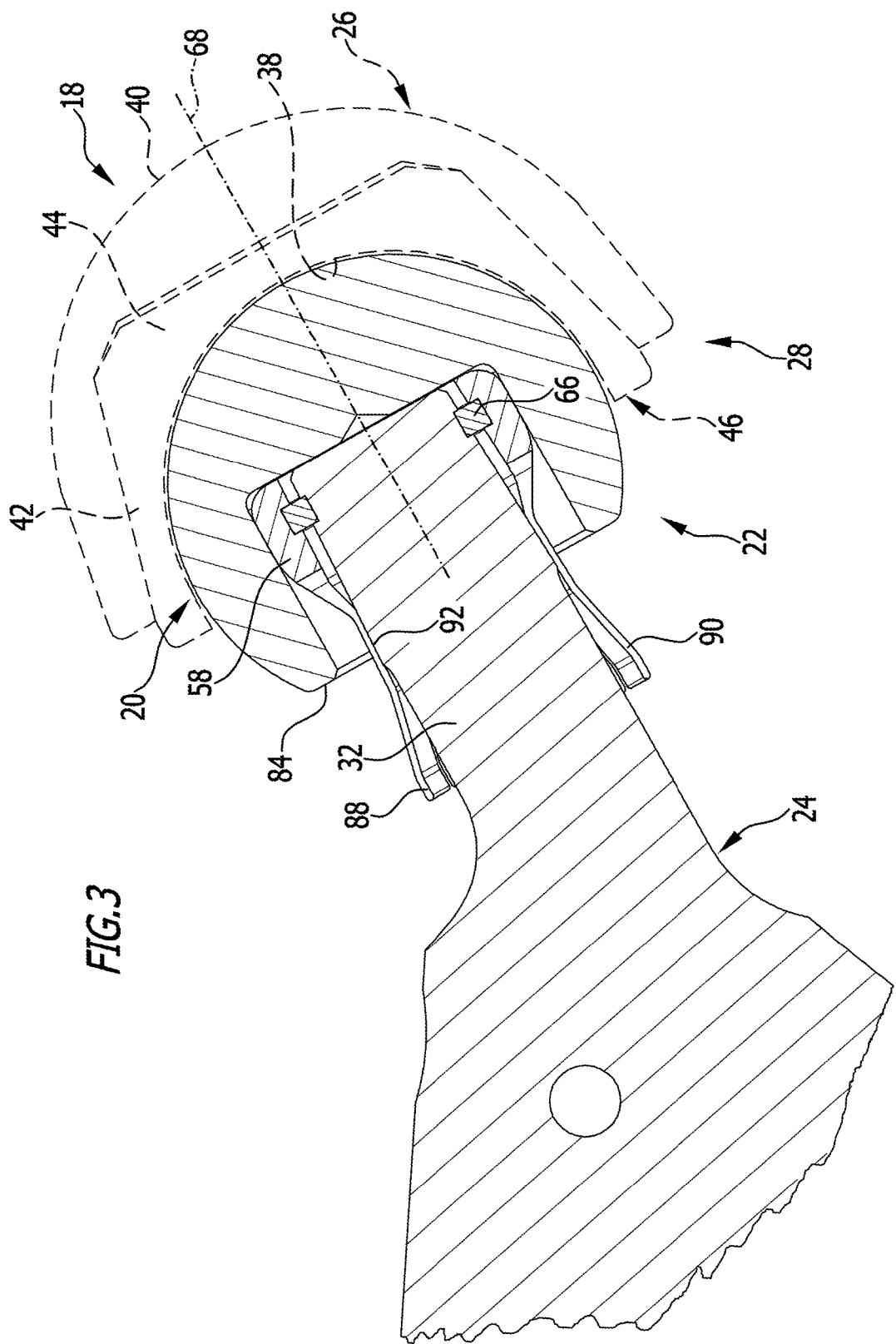
FIG. 3: a sectional view along the line 3-3 in FIG. 1.
Figure 4:
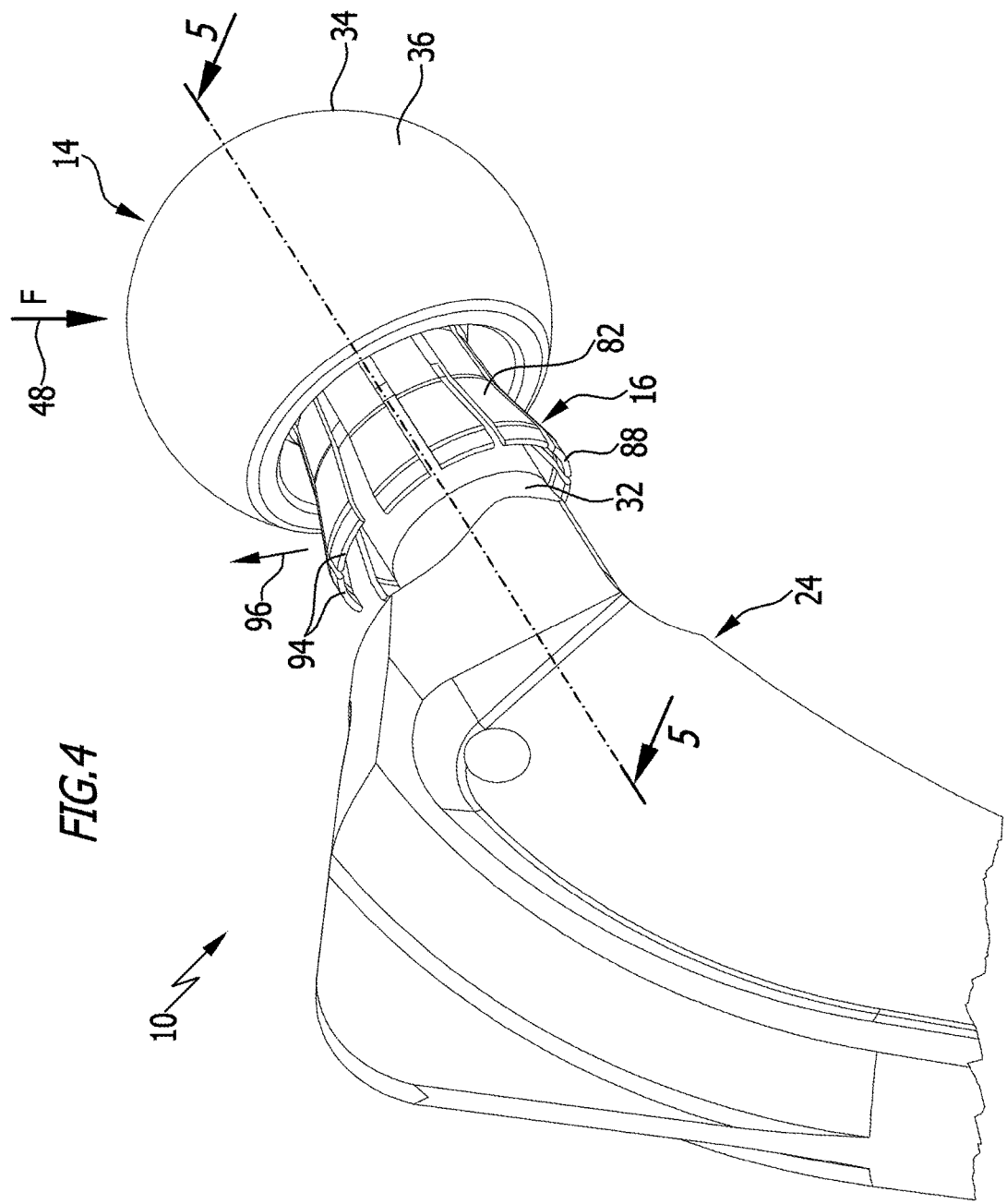
FIG. 4: an enlarged partial view of the arrangement depicted in FIG. 1 wherein there is a force effective on the sample joint element.
Figure 5:
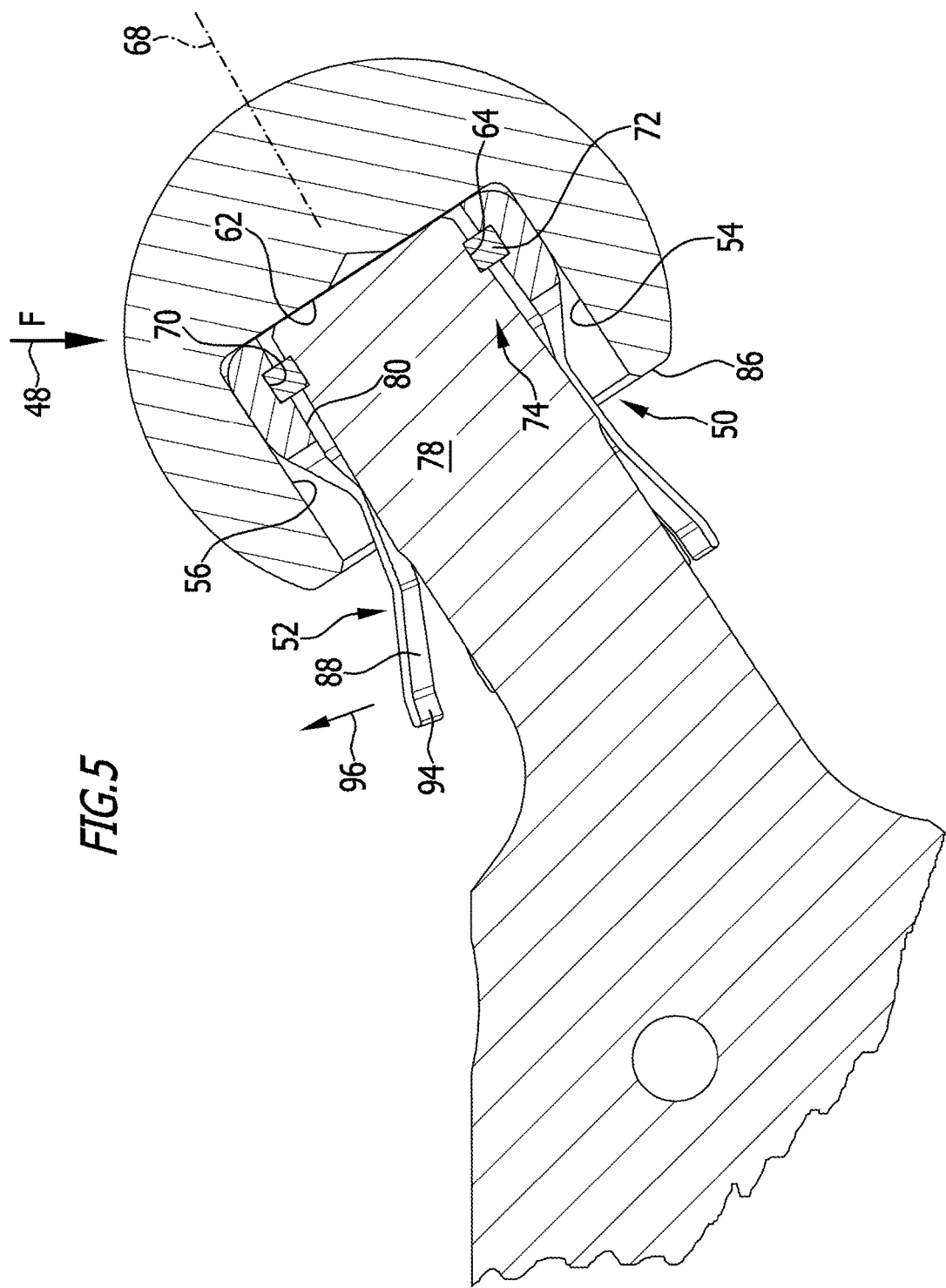
FIG. 5: a sectional view along the line 5-5 in FIG. 4.

If, as schematically illustrated in FIG. 3, the sample joint element 14 is brought into engagement with the socket insert 42 which forms a joint element 44, then, overall, a sample ball joint 46 is temporarily formed.

For the purposes of measuring and/or indicating a force effective on the sample joint surface 36 or a partial component of the force 48 effective on the sample joint surface 36, the measuring instrument 12 comprises a measuring device 50 which cooperates with the sample joint element 14 and an indicating device 52.

The sample ball joint 34 comprises a recess 54 in the form of a hollow cylindrical blind hole 56. The coupling element 16 comprises a hollow cylindrical ring 58 which is a press fit in the recess 54 and the proximal end face 60 thereof rests on the bottom 62 of the blind hole 56.

A peripheral annular groove 64 into which a clamping element 66 is inserted is formed on the neck 32. The clamping element 66 engages in an annular groove 70 which is open towards a longitudinal axis 68 of the coupling element and serves for coupling the prosthesis part 24 to the measuring instrument 12, namely, to the coupling element 16 thereof. The clamping element 66 is in the form of a clamping ring 72 which is preferably resilient and/or flexible in order to simplify the process of engaging with both the prosthesis part 24 and the coupling element 16.

The measuring instrument 12 comprises a measuring instrument coupling device 74 for temporarily coupling it in force- and/or positive-locking manner to a coupling device 76 of the prosthesis part 24. The coupling device 76 comprises the neck 32 and the annular groove 64 as well as the clamping element 66. In particular, the measuring instrument coupling device 74 comprises the annular groove 70.

If a medical instrument in the form of a rasp is used instead of the shaft 30, then these parts of the coupling device 76 form the instrument coupling device mentioned above.

Alternatively, the coupling element 16 could also be formed in one piece with the medical instrument, for example, in the form of a rasp shaft or a rasp.

The coupling device 76 comprises a coupling projection 78 which in essence is formed by the neck 32, the measuring instrument coupling device 74 comprises a coupling seating 80 which substantially corresponds to the coupling projection 78. The coupling projection 78 is thereby arranged or formed on the prosthesis part 24 or alternatively on the instrument, the coupling seating 80 on the measuring instrument 12. Alternatively, the coupling seating could also be arranged or formed on the prosthesis part or on the instrument, the coupling projection on the measuring instrument.

The indicating device 52 comprises a plurality of indicating elements 82 as well as a reference element 84 in the form of a flat end face 86 which faces away from the sample joint element 14 in the distal direction. The indicating elements 82 and the reference element 84 are moveable relative to each other.

The indicating elements 82 are substantially in the form of concavely curved strips 90 which are directed away from the longitudinal axis 68 of the coupling element and comprise a short contact section 92 with which they abut against the neck 32. The strips 90 extend substantially parallel to the longitudinal axis 68 of the coupling element and are formed in one piece with the coupling element 16. They extend away from the ring 58 out of the recess 54.

Figure 2:
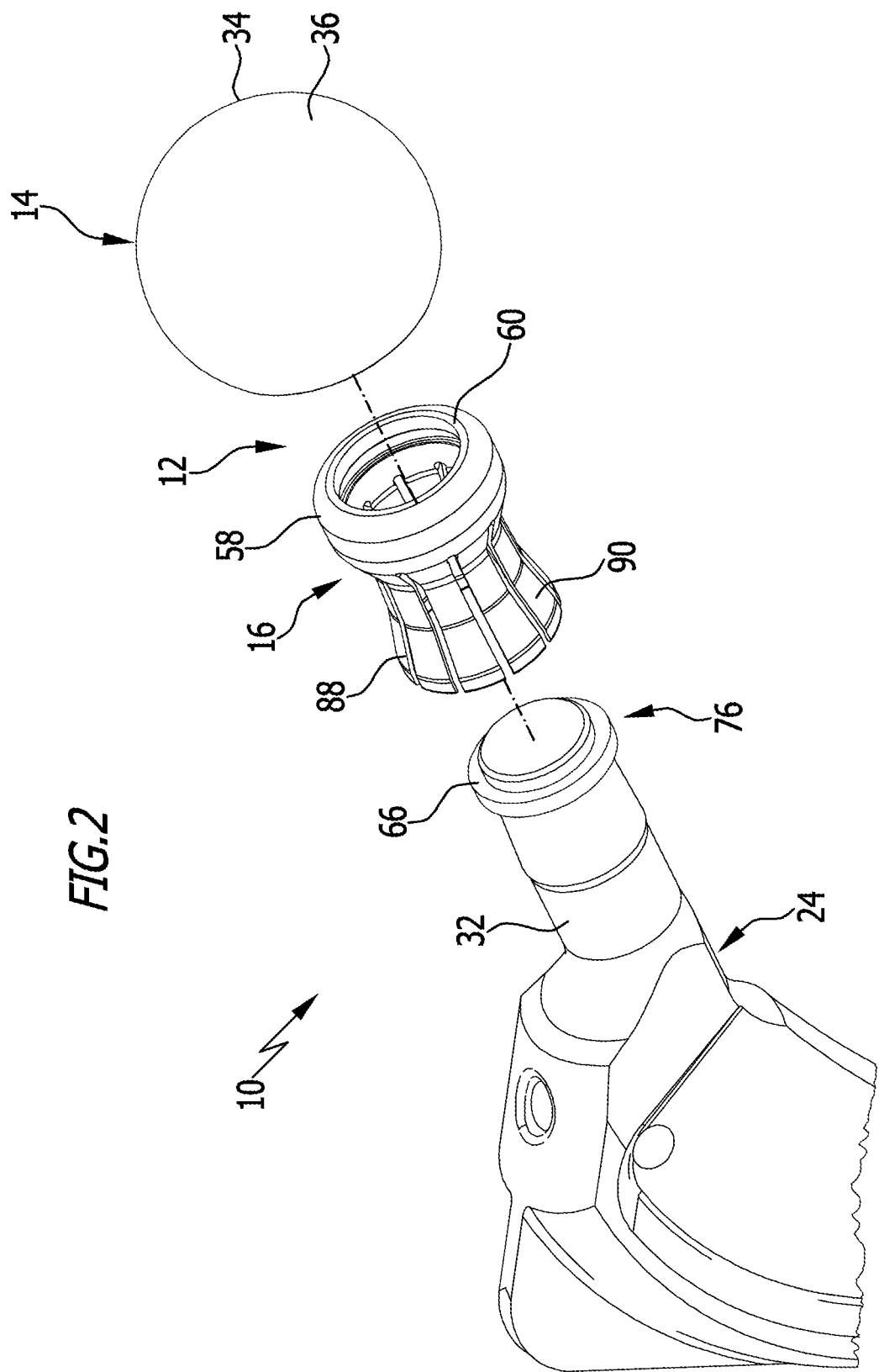
FIG. 2: a partial view of the arrangement depicted in FIG. 1 in the form of an exploded illustration.

In a basic position as is illustrated schematically in FIGS. 1 to 3, the lamellas 80 surround the longitudinal axis 68 of the coupling element concentrically.

If a force 48 is exerted on the sample joint surface 36, then the sample joint element 14 moves with the coupling element 16 relative to the neck 32 in such a manner that at least one of the lamellas 88 will be deformed in such a way that the free end 94 thereof indicates in a direction 96 which is substantially opposite to the direction of the force 48. In dependence on the effective direction of the force 48, two or more lamellas 88 may also be deformed in the manner described as is illustrated exemplarily in FIG. 4.

Due to the deflection of the indicating elements 82, the surgeon can immediately deduce the direction from which the force 48 is coming and, in dependence on the size of the deflection of the indicating elements 82 relative to the reference element 84, the magnitude of the force 48.

Figure 6:
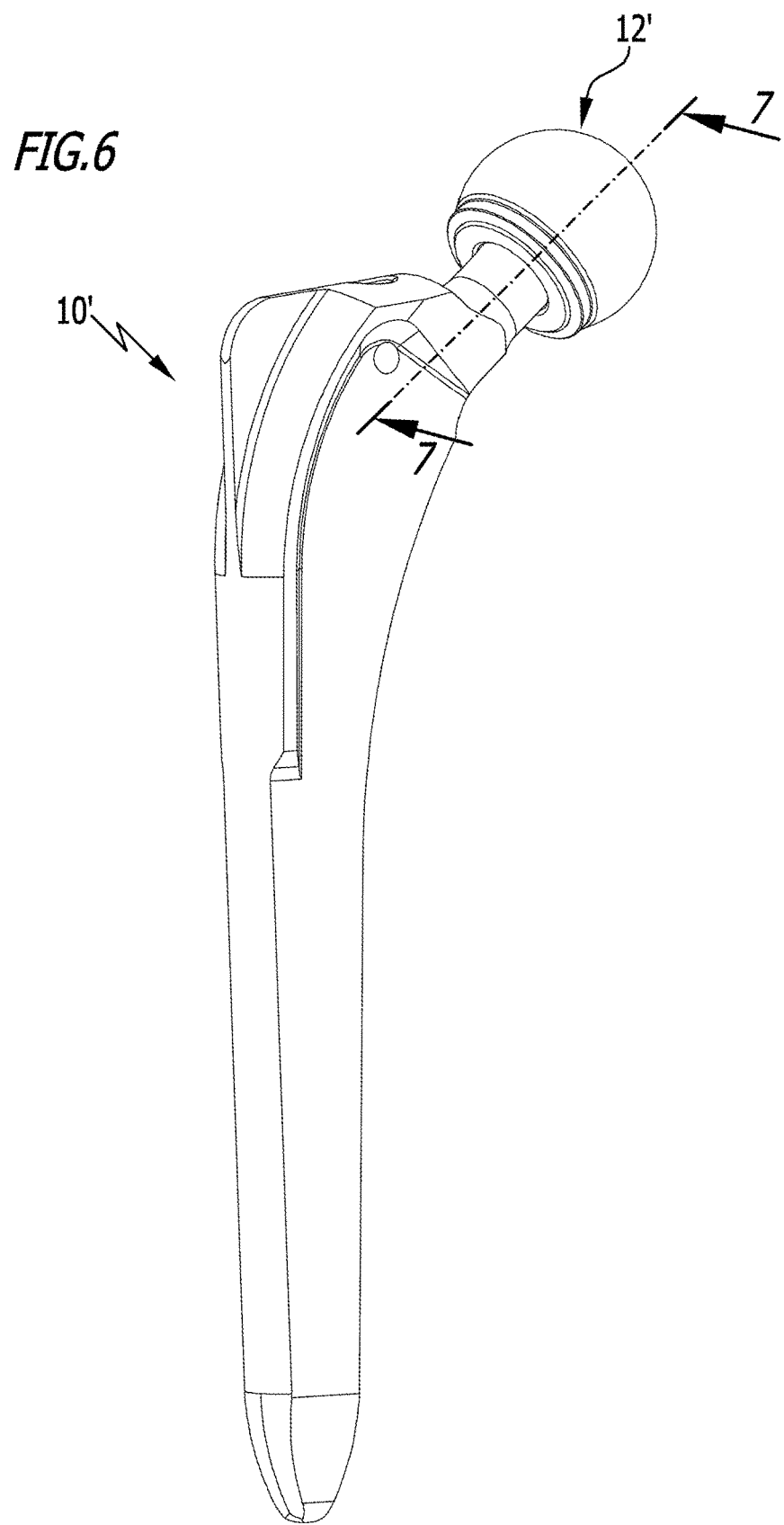
FIG. 6: a schematic perspective view of a second exemplary embodiment of a medical measuring system.
Figure 7:
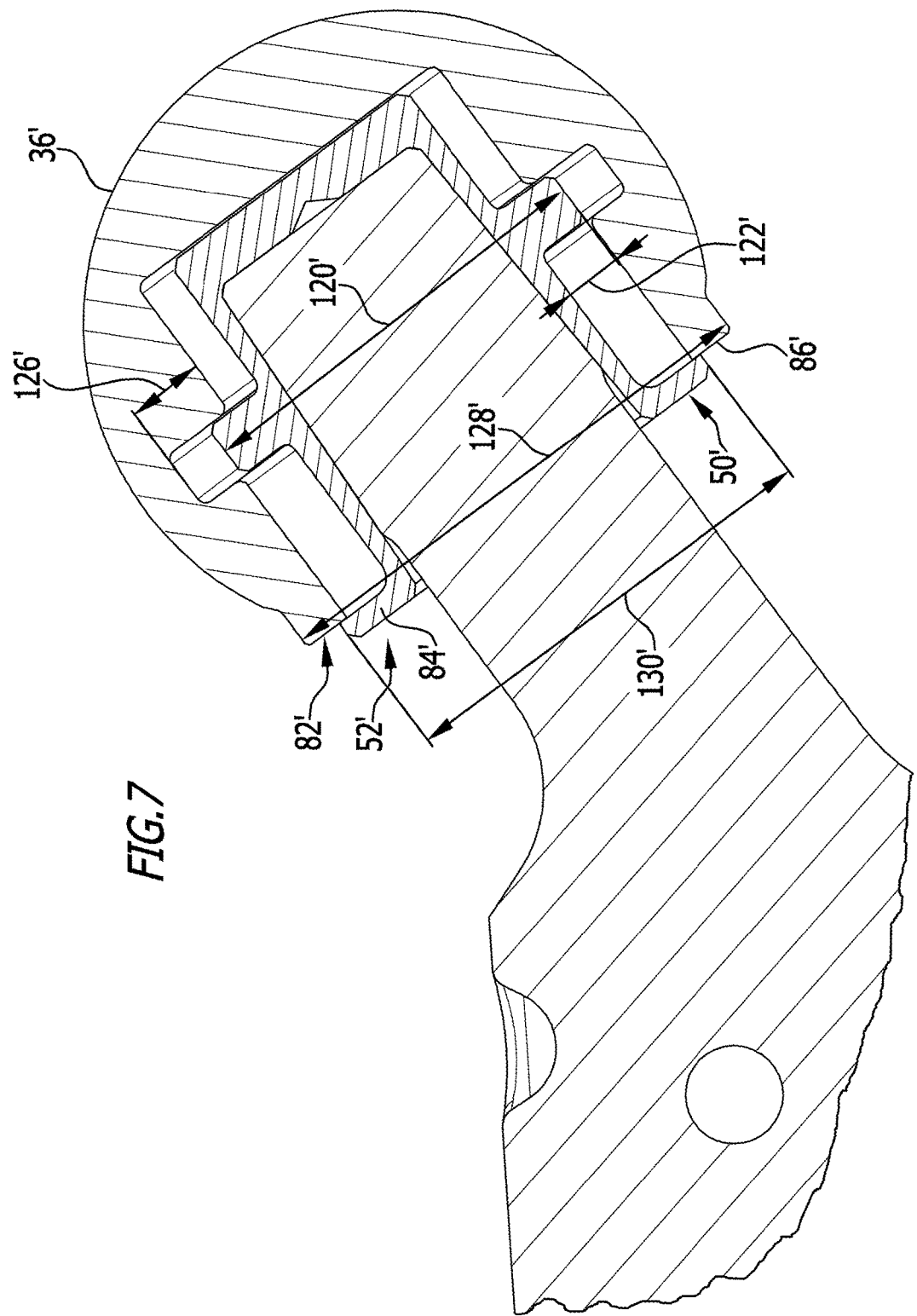
FIG. 7: a sectional view along the line 7-7 in FIG. 6.
Figure 8:
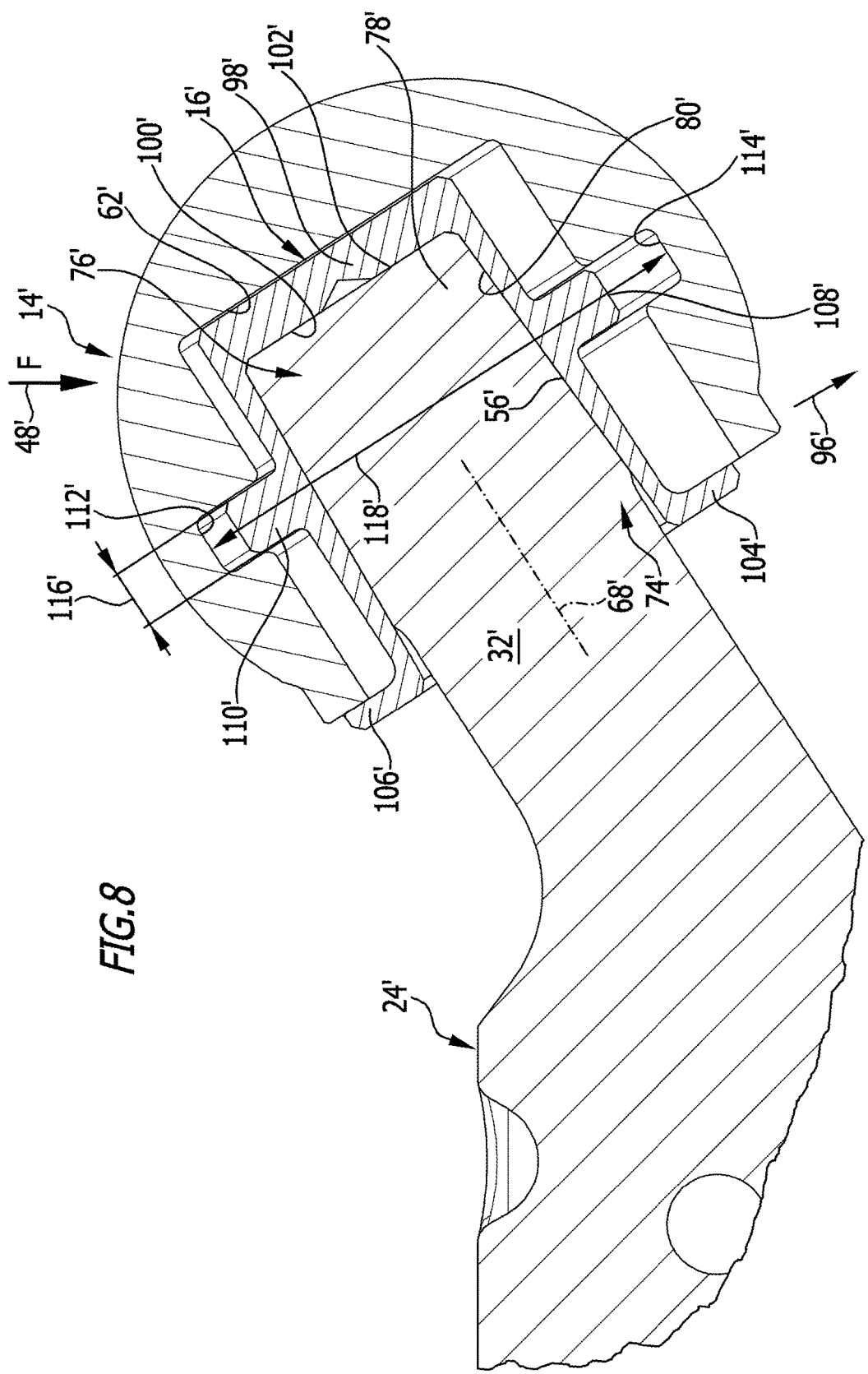
FIG. 8: a sectional view similar to FIG. 7, but wherein the sample joint element is deflected relative to the coupling element.
Figure 9:
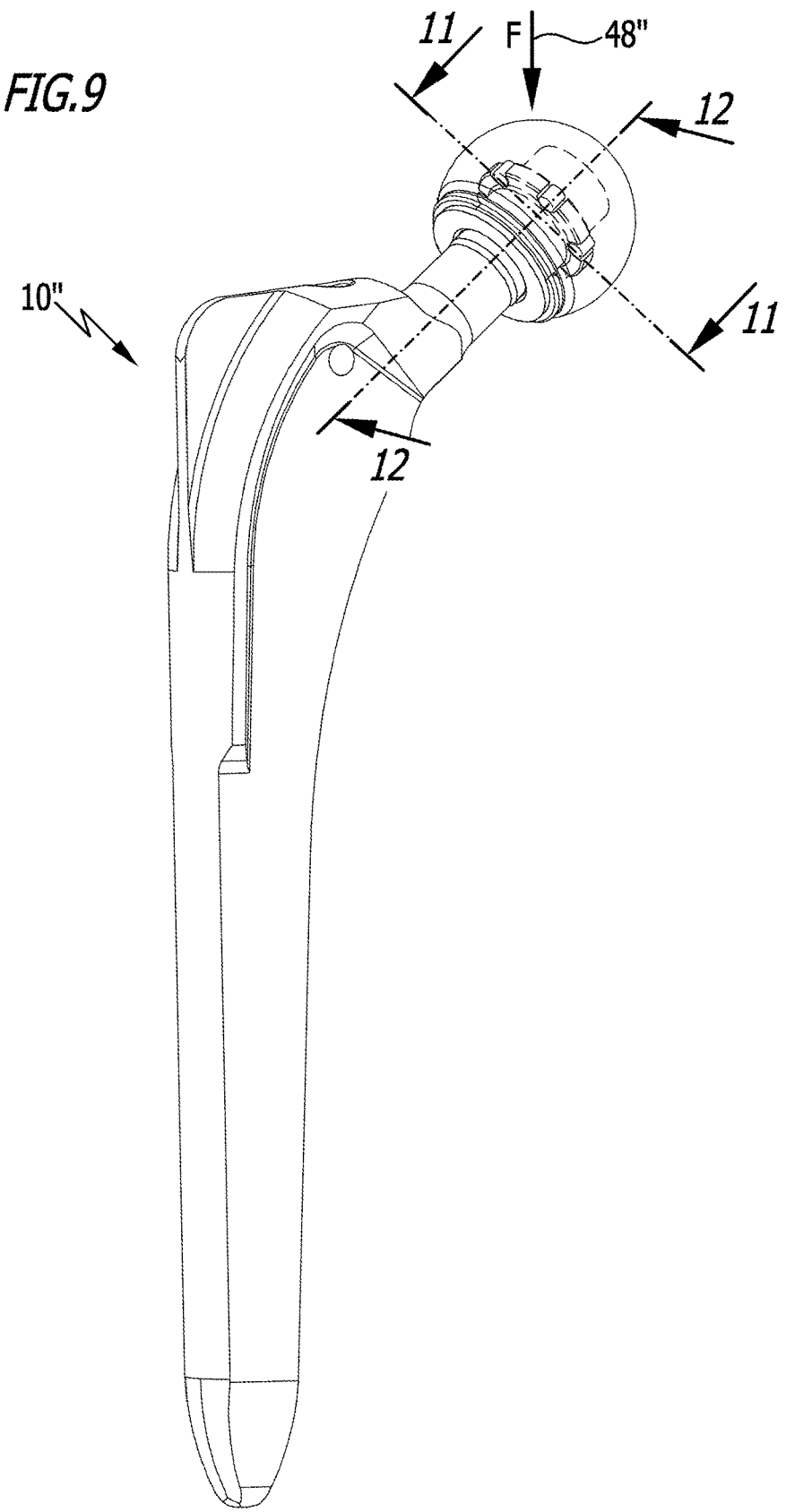
FIG. 9: a perspective, partially cut-away overall view of a third exemplary embodiment of a medical measuring system.
Figure 10:
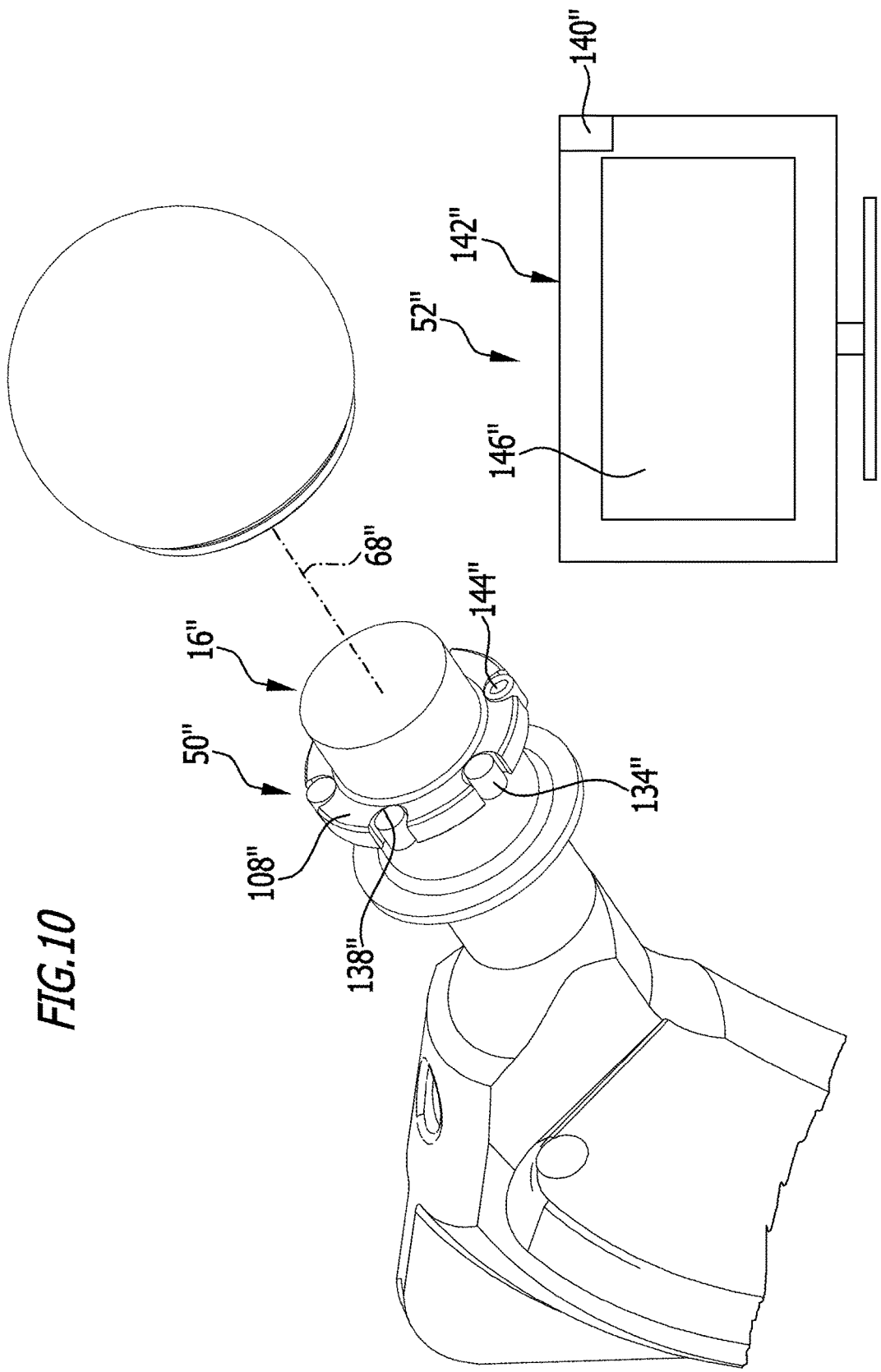
FIG. 10: a partial view of the arrangement depicted in FIG. 9 wherein the sample joint element is removed.
Figure 11:
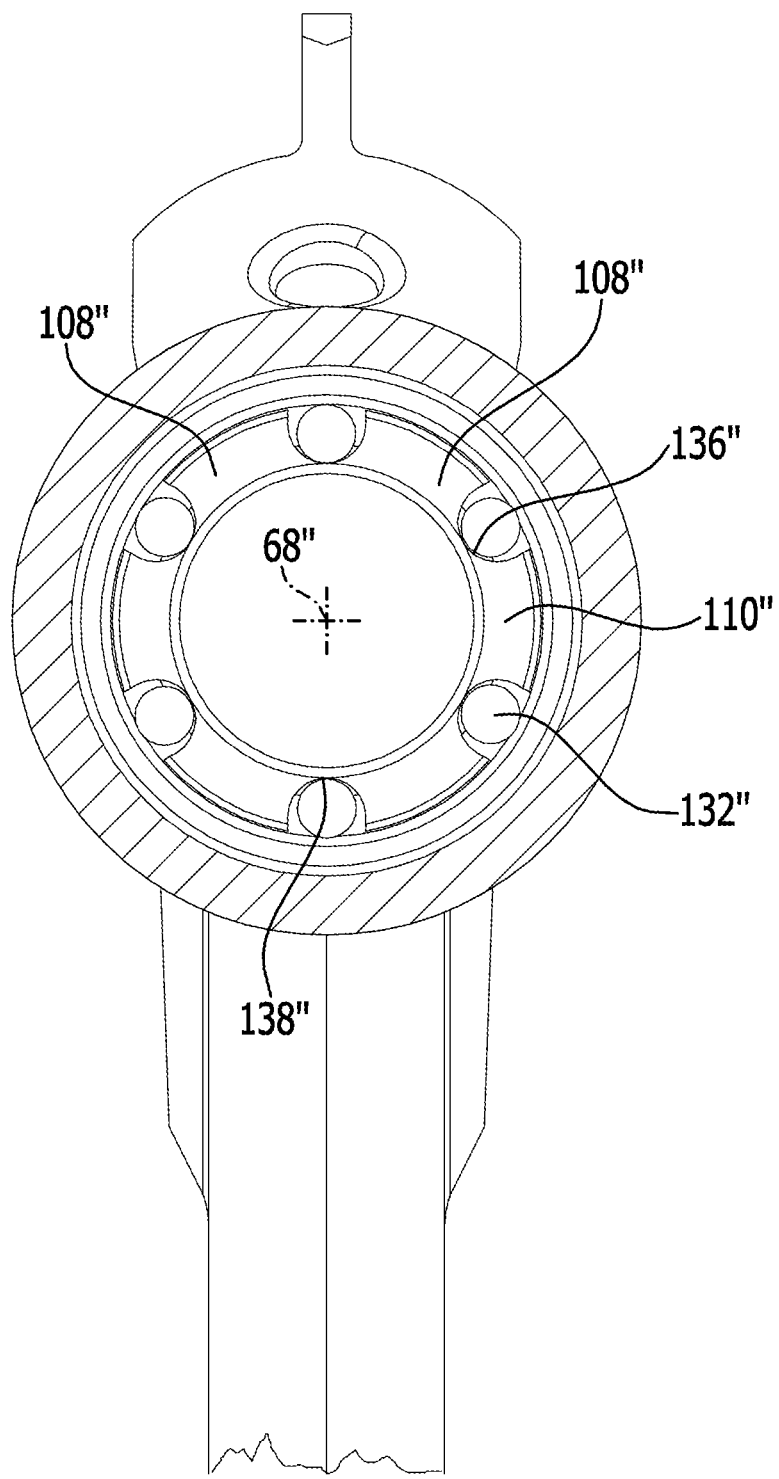
FIG. 11: a sectional view along the line 11-11 in FIG. 9.
Figure 12:
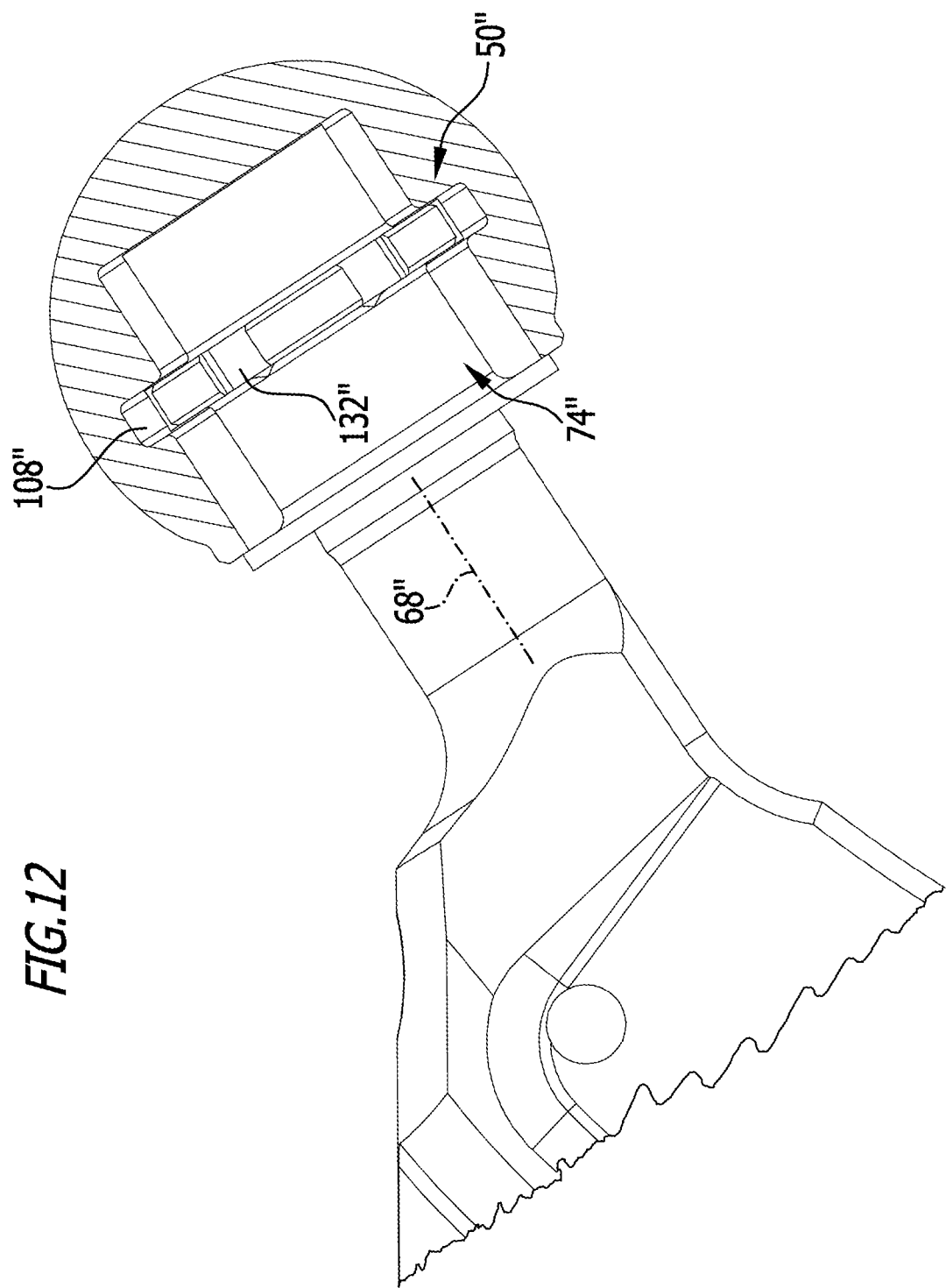
FIG. 12: a sectional view along the line 12-12 in FIG. 9.

A second exemplary embodiment of a medical force measuring system bearing the general reference symbol 10' is schematically illustrated in FIGS. 6 to 8. It differs from the measuring system 10 in essence by the construction of the measuring instrument 12'. Consequently, for the sake of clarity, all the parts and elements of the force measuring system 10' are designated hereinafter by identical reference symbols with the addition of a dash.

The prosthesis part 24' differs from the prosthesis part 24 only in that the neck 32' does not comprise an annular groove. It forms the coupling device 76' in the form of a coupling projection 78' which engages in the coupling seating 80' of the hollow cylindrical coupling element 16', the seating being in the form of a blind hole. A proximal end of the coupling element 16' is closed by a disk-like end-face wall 98'. A flat end face 102' of the neck 32' facing in the proximal direction impinges against the inner surface 100' thereof.

The coupling seating 80' forms a part of the measuring instrument coupling device 74'. The neck 32' is a press fit in the coupling seating 80'.

A distal end of the coupling element 16' is formed by a ring flange 104' which is directed away from the longitudinal axis 68' of the coupling element in the radial direction and defines a circular ring 106'. Furthermore, a further ring flange 108' directed away from the longitudinal axis 68' of the coupling element in the radial direction is formed on the coupling element 16' between the end-face wall 98' and the ring flange 104'. It forms a coupling member 110' which engages with a further coupling member 112' that is in the form of an annular groove 114' which is open in the direction towards the longitudinal axis 68' of the coupling element. The width 116' of the ring flange 108' and that of the annular groove 114' parallel to the longitudinal axis 68' of the coupling element are substantially identical.

The coupling element 16' engages in the blind hole 56' of the sample joint element 14' so that the end-face wall 98' rests on the bottom 62' of the blind hole 56'. Therein, in the position schematically illustrated in FIGS. 7 and 8, the ring flange 108' engages in the annular groove 114'. The minimum internal diameter 118' of the annular groove 114' is greater than the maximum external diameter 120' of the ring flange 108'. The height 122' of the ring flange 108' in the radial direction is somewhat greater than half the depth 126' of the annular groove 114' in the radial direction.

The coupling element 16' and the sample joint element 14' are axially fixed relative to each other with reference to the longitudinal axis 68' of the coupling element. The end face 86' of the sample joint element 14' facing in the distal direction in cooperation with the ring 106' forms a measuring device 50' as well as an indicating device 52' for measuring the force 48' that is effective on the sample joint element 14'. The end face 86' forms an indicating element 82', the ring 106' a reference element 84'. The ring 106' has an external diameter 130' which is smaller than the external diameter 128' of the end face 86'. Consequently, a part of the end face 86' is always visible independently of the relative position between the sample joint element 14' and the coupling element 16'.

In a basic position of the measuring instrument 12' such as is schematically illustrated in FIG. 7, both the end face 86' and the ring 106' are aligned coaxially with respect to the longitudinal axis 68' of the coupling element.

If a force 48' is effective on the sample joint element 14', then the latter is displaced relative to the coupling element 16' in a plane transverse to the longitudinal axis 68' of the coupling element. Consequently, the end face 86' that is visible in the basic position in the form of an annulus is deformed such as to be quasi non-circular since the ring 106' continues to cover the end face 86' on the side facing the force 48'. As a result, the end face 86' is more visible on the opposite side.

For example, the end face 86' can be coloured in a different colour than the sample joint surface 36' so that the indicating element 82' stands out more clearly from the reference element 84' and is recognizable by the surgeon. Due to the displacement of the sample joint element 14' and the coupling element 16' relative to each other, the surgeon can immediately ascertain the magnitude and/or the orientation of the force 48' on the basis of the deformation of the visible part of the end face 86'.

A third exemplary embodiment of a force measuring system designated by the general reference symbol 10" is illustrated exemplarily in FIGS. 9 to 12. The basic construction thereof corresponds to that of the force measuring system 10' and differs from the coupling element 16' of the force measuring system 10' only in the design of the coupling element 16". Consequently, to avoid repetition in regard to the construction and the arrangement of the basic structure of the force measuring system 10" reference is made to the explanations of the force measuring system 10' given above.

The coupling element 16" comprises a plurality of force measuring sensors 132", in particular exactly six, which are in the form of small cylinders 134" and are arranged in sensor seatings 136". The sensor seatings 136" are in the form of semi-cylindrical recesses 138" in the ring flange 108". The internal diameter defined by the recesses 138" is greater than the external diameter of the force measuring sensors 132". The recesses 138" are open away from the longitudinal axis 68" of the coupling element in the direction of the sample joint element 14'. The force measuring sensors 132" are thus arranged or held on the coupling member 110" of the coupling element 16".

The measuring device 50" thus comprises the plurality of force measuring sensors 132" for measuring the magnitude and/or direction of a force 48" that is effective on the sample joint element 14'.

In particular, the force measuring sensors 132" may be in the form of electronic force measuring sensors 132" for producing an electrical measuring signal. For the purpose of transferring the measuring signal to a receiving device 140" of a signal indicator device 142", the force measuring sensor 132" may comprise a transmitting device 144" for sending the measuring signal to the receiving device 140". Furthermore, the signal indicator device 142" can be arranged to evaluate and/or indicate the measuring signal. In particular, the signal indicator device 142" may comprise a screen 146". Transmission of the measuring signals from the transmitting device 144" to the receiving device 140" can be effected over cables or a non-cable connection. A non-cable connection may, in particular, be a transmission by means of Bluetooth or radio.

If the force 48" is effective on the sample joint element 14', then the direction and/or orientation of the force 48" can be determined by means of the measuring device 50" and the force measuring sensors 132" thereof. The evaluation of the measuring signals of the force measuring sensors 132" can, for example, be displayed for the surgeon on the screen 146" so that he will know how he needs to change a soft part situation in order to prevent a force imbalance on the joint prosthesis.

LIST OF REFERENCE SYMBOLS 10, 10', 10" force measuring system
12, 12', 12" measuring instrument
14, 14' sample joint element
16, 16', 16" coupling element
18 joint prosthesis
20 ball joint
22 partial component
24, 24' prosthesis part
26 prosthesis part
28 hip joint endoprosthesis
30 shaft
32, 32' neck
34 sample joint head
36, 36' sample joint surface
38 joint surface
40 acetabulum
42 socket insert
44 joint element
46 sample ball joint
48, 48', 48" force
50, 50', 50" measuring device
52, 52" indicating device
54 recess
56, 56' blind hole
58 ring
60, 60' end face
62, 62' bottom
64 annular groove
66 clamping element
68, 68', 68" longitudinal axis of the coupling element
70 annular groove
72 clamping ring
74, 74', 74" measuring instrument coupling device
76, 76' coupling device
78, 78' coupling projection
80, 80' coupling seating
82, 82' indicating element
84, 84' reference element
86, 86' end face
88 lamella
90 strip
92 contact section
94 end
96 direction
98' end-face wall
100' inner side
102' end face
104 ring flange
106' ring
108' ring flange
110' coupling member
112' coupling member
114' annular groove
116' width
118' internal diameter
120' external diameter
122' height
126' depth 128' external diameter
130' external diameter
132" force measuring sensor
134" cylinder
136" sensor seating
138" recess
140" receiving device
142" signal indicator device
144" transmitting device
146" screen

What is claimed is:

1. Medical force measuring system for measuring a force that is effective between two prosthesis parts of a joint prosthesis, the two prosthesis parts being connected to one another in an articulated manner, the joint prosthesis comprising a ball joint or a partial component thereof, which force measuring system comprises:
   a measuring instrument, the measuring instrument comprising:
      a sample joint element having a sample joint surface, the sample joint element being formed in correspondence with a first joint element that forms a part of the ball joint and comprises a joint surface that is formed in correspondence with the sample joint surface and is moveable into engagement therewith for forming a sample ball joint, and
      an indicating device arranged or formed on the measuring instrument which cooperates with the sample joint element for indicating a force that is effective on the sample joint surface or a partial component of the force that is effective on the sample joint surface,
   wherein:
   the measuring instrument further comprises a coupling element;
   the medical force measuring system further comprises a medical instrument which is couplable to the measuring instrument,
   the medical instrument further comprises an instrument coupling device,
   the instrument coupling device comprises a clamping element which is moveable into engagement in at least one of a force-locking and a positive-locking manner with the prosthesis part or the medical instrument on the one hand and with the coupling element on the other hand, and
   the clamping element is in the form of a clamping ring which, in a clamping position, engages in at least one of (a) an annular groove in the prosthesis part or in the medical instrument on the one hand, and (b) an annular groove in the coupling element on the other hand.

2. The medical force measuring system in accordance with claim 1, wherein at least one of:
   (a) the measuring instrument further comprises a measuring instrument coupling device for temporarily coupling in at least one of a force-locking and a positive-locking manner to a coupling device of the prosthesis part of the joint prosthesis or the medical instrument, and
   (b) the medical instrument comprises the measuring instrument.

3. The medical force measuring system in accordance with claim 1, wherein at least one of:
   (a) the medical instrument is in the form of a rasp or a rasp shaft,
   and
   (b) the measuring instrument further comprises a measuring instrument coupling device, wherein the instrument coupling device is moveable:
      (i) into engagement with the measuring instrument coupling device in at least one of a force-locking and a positive-locking manner,
   or
      (ii) into engagement with the measuring instrument coupling device in at least one of a force-locking and a positive-locking manner, the instrument coupling device or the measuring instrument coupling device is in the form of a coupling projection and wherein the respective other coupling device is in the form of a coupling seating corresponding to the coupling projection.

4. The medical force measuring system in accordance with claim 2, wherein:
   the measuring instrument further comprises the measuring instrument coupling device, wherein the instrument coupling device is moveable into engagement with the measuring instrument coupling device in at least one of a force-locking and a positive-locking manner,
   the instrument coupling device or the measuring instrument coupling device is in the form of a coupling projection and wherein the respective other coupling device is in the form of a coupling seating corresponding to the coupling projection, and
   the coupling projection is arranged or formed on the prosthesis part or on the medical instrument and the coupling seating is arranged or formed on the measuring instrument, or wherein the coupling seating is arranged or formed on the prosthesis part or on the medical instrument and the coupling projection is arranged or formed on the measuring instrument.

5. The medical force measuring system in accordance with claim 1, further comprising a prosthesis part of the joint prosthesis which is couplable temporarily to the measuring instrument.

6. The medical force measuring system in accordance with claim 1, wherein the sample joint element is in the form of a sample joint head or in the form of a socket insert of a hip joint prosthesis.

7. A medical force measuring system for measuring a force that is effective between two prosthesis parts of a joint prosthesis, the two prosthesis parts being connected to one another in an articulated manner, the joint prosthesis comprising a ball joint or a partial component thereof, which force measuring system comprises:
   a measuring instrument, the measuring instrument comprising:
      a sample joint element having a sample joint surface, the sample joint element being formed in correspondence with a first joint element that forms a part of the ball joint and comprises a joint surface that is formed in correspondence with the sample joint surface and is moveable into engagement therewith for forming a sample ball joint, and
      an indicating device arranged or formed on the measuring instrument which cooperates with the sample joint element for indicating a force that is effective on the sample joint surface or a partial component of the force that is effective on the sample joint surface,
   wherein:
   the indicating device comprises at least one indicating element and at least one reference element, the at least one indicating element and the at least one reference element are arranged or formed such as to be moveable relative to each other, the measuring instrument further comprises a coupling element, and the indicating device comprises a plurality of indicating elements which are at least one of deflectable from a basic position and are temporarily deformable as a result of an application of force to at least one of the sample joint element and the coupling element.

8. The medical force measuring system in accordance with claim 1, wherein the sample joint element and the coupling element are arranged to be moveable relative to each other or are mounted on one another or are formed such as to be moveable relative to each other.

9. The medical force measuring system in accordance with claim 1, wherein the sample joint element and the coupling element are arranged or formed to be at least one of displaceable and rotatable relative to each other.

10. The medical force measuring system in accordance with claim 7, wherein:

the medical force measuring system further comprises a medical instrument which is couplable to the measuring instrument, wherein the medical instrument further comprises an instrument coupling device, wherein the instrument coupling device comprises a clamping element which is moveable into engagement in at least one of a force-locking and a positive-locking manner with the prosthesis part or the medical instrument on the one hand and with the coupling element on the other hand, and the clamping element is in the form of a clamping ring which, in a clamping position, engages in at least one of (a) an annular groove in the prosthesis part or in the medical instrument on the one hand, and (b) an annular groove in the coupling element on the other hand.

11. The medical force measuring system in accordance with claim 1, wherein the indicating device comprises at least one indicating element and at least one reference element and wherein the at least one indicating element and the at least one reference element are arranged or formed such as to be moveable relative to each other.

12. The medical force measuring system in accordance with claim 7, wherein the coupling element comprises a measuring instrument coupling device for temporarily coupling to a prosthesis part of the joint prosthesis or to the medical instrument.

13. The medical force measuring system in accordance with claim 7, wherein the plurality of indicating elements is arranged or formed around the coupling seating in a circumferential direction.

14. The medical force measuring system in accordance with claim 11, wherein the at least one indicating element is in the form of an annular surface on the sample joint element or on the coupling element, and wherein the at least one reference element is in the form of a ring which is of smaller diameter than the annular surface and at least partly covers it.

15. The medical force measuring system in accordance with claim 14, wherein the annular surface is in the form of a flat end face which faces away from the sample joint element and surrounds a recess of the sample joint element with which the coupling element engages, and wherein the coupling element comprises a ring flange which surrounds the coupling seating and is directed radially away from a longitudinal axis of the coupling seating and also forms the ring.

16. The medical force measuring system in accordance with claim 1, wherein:

at least one of the sample joint element is formed in one piece manner and the coupling element is formed in one piece manner.

17. The medical force measuring system in accordance with claim 1, wherein the measuring instrument further comprises a measuring device which cooperates with the sample joint element for measuring a force that is effective on the sample joint surface or a partial component of the force that is effective on the sample joint surface.

18. Medical force measuring system for measuring a force that is effective between two prosthesis parts of a joint prosthesis, the two prosthesis parts being connected to one another in an articulated manner, the joint prosthesis comprising a ball joint or a partial component thereof, which force measuring system comprises:

a measuring instrument, the measuring instrument comprising:

a sample joint element having a sample joint surface, the sample joint element being formed in correspondence with a first joint element that forms a part of the ball joint and comprises a joint surface that is formed in correspondence with the sample joint surface and is moveable into engagement therewith for forming a sample ball joint, an indicating device arranged or formed on the measuring instrument which cooperates with the sample joint element for indicating a force that is effective on the sample joint surface or a partial component of the force that is effective on the sample joint surface, and a coupling element, the coupling element comprising a measuring instrument coupling device, wherein at least one of:

a) the sample joint element and the coupling element are arranged or formed to be at least one of displaceable and rotatable relative to each other, and b) the medical force measuring system further comprises a medical instrument which is couplable to the measuring instrument, the medical instrument further comprises an instrument coupling device, and the instrument coupling device comprises a clamping element which is moveable into engagement in at least one of a force-locking and a positive-locking manner with the prosthesis part or the medical instrument on the one hand and with the coupling element on the other hand.

19. The medical force measuring system in accordance with claim 1, wherein:

the indicating device comprises a plurality of indicating elements which are at least one of deflectable from a basic position and are temporarily deformable as a result of an application of force to at least one of the sample joint element and the coupling element.

* * * * *